United States Patent [19]

Ishida

[11] Patent Number: 5,215,091
[45] Date of Patent: Jun. 1, 1993

[54] LITHOTRITY APPARATUS HAVING A MISSED-SHOT PREVENTIVE FUNCTION

[75] Inventor: Akinori Ishida, Kawasaki, Japan

[73] Assignee: Kabushiki Kaisha Toshiba, Kawasaki, Japan

[21] Appl. No.: 707,759

[22] Filed: May 30, 1991

[30] Foreign Application Priority Data

May 31, 1990 [JP] Japan .................................. 2-142001

[51] Int. Cl.$^5$ ............................................ A61B 17/22
[52] U.S. Cl. ............................ 128/660.03; 128/24 EL
[58] Field of Search ............... 128/660.03, 24 EL, 804

[56] References Cited

U.S. PATENT DOCUMENTS

| | | | |
|---|---|---|---|
| 4,526,168 | 7/1985 | Hassler et al. | 128/303 R |
| 4,658,828 | 4/1987 | Dory | 128/660 |
| 4,771,787 | 9/1988 | Wurster et al. | 128/660.03 |
| 4,803,995 | 2/1989 | Ishida et al. | 128/660.01 |
| 4,986,259 | 1/1991 | Aida et al. | 128/660.03 |
| 5,076,277 | 12/1991 | Iwana et al. | 128/660.03 |
| 5,078,143 | 1/1992 | Okazaki et al. | 128/660.03 |

FOREIGN PATENT DOCUMENTS 2587893 4/1987 France .

*Primary Examiner*—Ruth S. Smith
*Attorney, Agent, or Firm*—Oblon, Spivak, McClelland, Maier & Neustadt

[57] ABSTRACT

A lithotrity apparatus of this invention sends a low-pressure wave into a body continuously, at an interval shorter than an irradiating interval predetermined as an irradiating rate of an impulse from an impulse source. The low-pressure wave serves to discriminate coincidence and non-coincidence of a position of a focal point and that of a stone. When the intensity of the impulse received by a piezocrystal is at a predetermined threshold or higher, it is determined that the focal point coincides with the stone, and an impulse is radiated. Radiation of the impulse and a low-pressure wave is stopped during a time period corresponding to the predetermined radiation interval starting from the moment of impulse radiation. More specifically, the apparatus uses a piezocrystal as the impulse source. The piezocrystal is driven by a pulse generator and and a low-power supply when a low-pressure wave of a interval shorter than the predetermined irradiating interval is generated. The echo of the low-pressure wave is received. When a comparing circuit determines that the echo intensity is a threshold or more, the piezocrystal is switched to a high-power supply and is driven by a high-power pulse, thereby radiating an impulse. At this time, driving of the piezocrystal by the high-power source is kept stopped by an echo rate counter for a time interval corresponding to a predetermined irradiating interval, that is, until a subsequent cycle. Also, the pulse generator is stopped to sending a low-pressure wave by a switching operation of a switch. The apparatus operates in the above manner and is practiced by the above constituent elements.

9 Claims, 3 Drawing Sheets

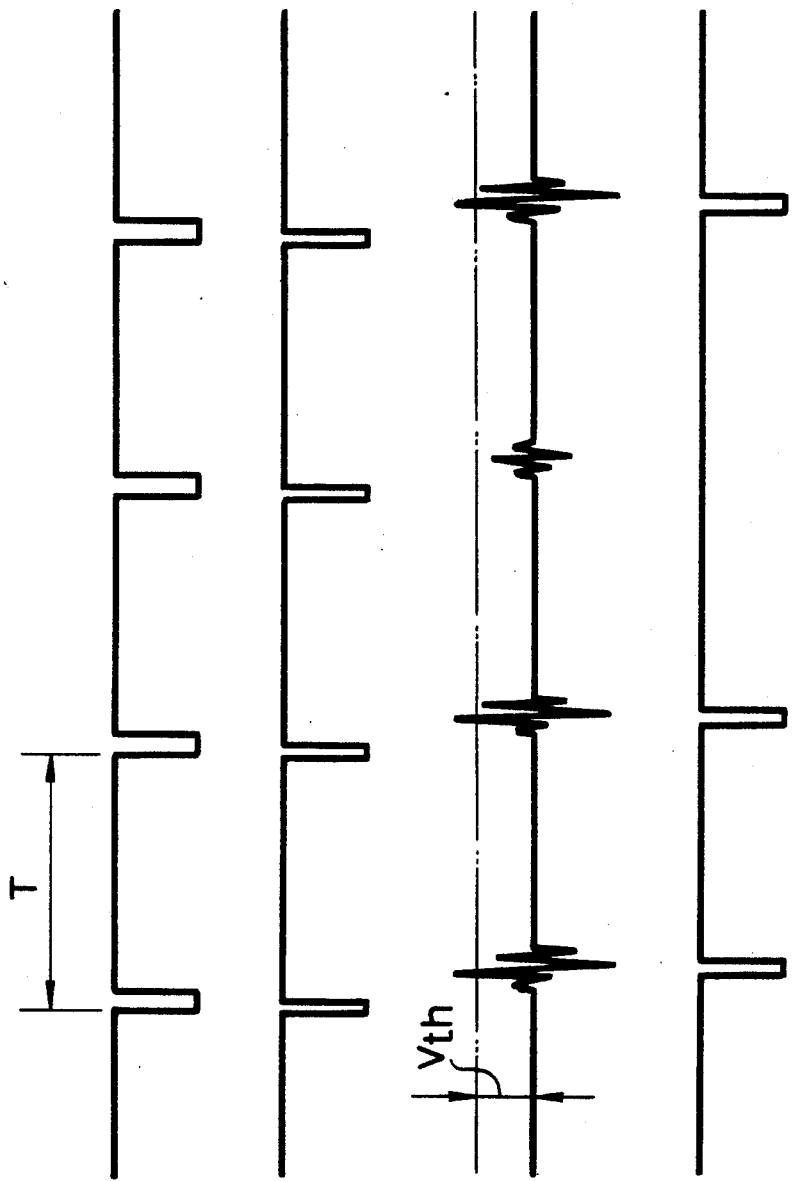

LITHOTRITY APPARATUS HAVING A MISSED-SHOT PREVENTIVE FUNCTION

BACKGROUND OF THE INVENTION

1. Field of the Invention

The present invention relates to a lithotrity apparatus for externally irradiating a stone in a patient's body with a focused impulse emitted from an impulse source such as a piezoelectric device to perform lithotrity treatment, and more particularly, to a lithotrity apparatus having a missed-shot preventive function which prevents an impulse from erroneously irradiating a normal tissue.

2. Description of the Related Art

In treatment of mainly a renal calculus, a method of externally irradiating a stone in a body with a focused impulse to pulverize the stone for non-invasive treatment has recently begun to be widely used. Treatment methods which use underwater discharge, electromagnetic induction, micro explosion, a piezoelectric device and the like as an impulse source are known well.

According to one that uses a piezoelectric device, among these methods, an echo sent from a focal zone of the impulse can be received by the piezoelectric device which is also used for impulse generation. A technique which utilizes this function to prevent missed-shot during treatment is conventionally proposed (for example, refer to Japanese Patent Application Nos. 60-191250 and 61-149562). According to a lithotrity apparatus which employs this technique, immediately before an intense impulse for lithotrity treatment is emitted, an ultrasonic wave weaker than that (to be referred to as a low-pressure wave hereinafter) is sent and received. When an intense echo is returned, it is determined that the focal point coincides with the stone. Then, the piezoelectric device is driven by a high voltage to irradiate a target, i.e., the stone with an intense impulse.

FIGS. 3(a) to 3(d) are timing charts for explaining an example of a missed-shot preventive method in accordance with a conventional technique. FIG. 3(a) is a timing chart of an irradiating rate pulse having an impulse irradiating interval T; FIG. 3(b) is an irradiating timing chart of a low-pressure wave; FIG. 3(c) is a timing chart of a received echo; and FIG. 3(d) is a timing chart of an impulse irradiating timing.

The echo of FIG. 3(c) is compared with a threshold Vth. The piezoelectric device is driven by a high voltage only when the echo intensity is the threshold Vth or more. Then, an impulse is emitted at a timing as shown in FIG. 3(d). When the echo intensity is lower than Vth, an impulse for lithotrity is not radiated and must wait until the irradiating timing of the subsequent comparison cycle. When such control is performed, lithotrity treatment can be performed without a missed-shot in which a normal tissue other than the stone is irradiated with the impulse. As a result, a side-effect on the patient caused by the lithotrity treatment is decreased.

When the impulse irradiating interval T is excessively short, the patient may sometimes feel pain. Also, since the pulverization pressure can be decreased due to cavitation and the like, the impulse irradiating rate of about 1 to 3 Hz (namely, 1 to 0.33 shot/sec.) is usually employed. When the irradiating rate is, e.g., 1 Hz, the irradiating interval T is 1 second. According to the conventional missed-shot preventive technique described above, the low-pressure wave is sent and received every T second, and coincidence of the focal point (irradiating point) with the stone (i.e., target) is determined from the intensity of the received echo. Therefore, if the focal point and the stone do not instantaneously coincide, radiation must wait for another T second. Impulse lithotrity treatment is generally performed by radiating an impulse onto a target stone several hundreds to several thousands of times or more. Therefore, if the focal point and the stone do not often coincide during treatment, as described above, an accumulated wait time is long and thus cannot be neglected. Time required for lithotrity treatment becomes very long due to the accumulated wait time.

As described above, according to the missed-shot preventive method of the conventional lithotrity apparatus, a low-pressure wave is sent and received between time points corresponding to the impulse irradiating interval, thereby checking whether or not the focal point and the position of the stone coincide with each other. Impulse radiation is controlled based on the determination result of coincidence or non-coincidence. Therefore, if the focal point and the stone do not coincide during a certain comparison cycle, a time until a subsequent cycle is wasted, resulting in a prolonged treatment time for lithotrity.

SUMMARY OF THE INVENTION

It is an object of the present invention to provide a lithotrity apparatus which is free from a missed-shot of an impulse to a normal tissue other than a stone, and in which a wait time until radiation occurring when a focal point does not coincide with a stone is shortened, so that lithotrity treatment can be completed within the shortest period of time.

In order to solve this problem, the apparatus of the present invention has a characteristic as follows. A low-pressure wave for discriminating coincidence/non-coincidence of the focal point and the stone is sent into a patient's body at a shorter interval than an irradiating interval predetermined as the impulse irradiating rate, and the echo of the low-pressure wave is received. When the echo intensity is higher than a predetermined threshold, it is determined that the focal point and the stone coincide, and an impulse is emitted. A subsequent impulse radiation operation is prohibited immediately after this until a time corresponding to the predetermined irradiating interval elapses.

More specifically, according to the apparatus of the present invention, when a piezoelectric device is used as the impulse source, the piezoelectric device is driven by a low-power pulse at a time interval shorter than a predetermined irradiating interval to send a low-pressure wave into a patient's body, and the echo is received. When the echo intensity is higher than the threshold, the piezoelectric device is driven by a high-power pulse to emit an impulse. When the impulse is emitted, driving of the piezoelectric by a high-power pulse is stopped until a time corresponding to the predetermined irradiating interval elapses.

As described above, the impulse irradiating interval is predetermined considering the patient's pain and the lithotrity efficiency. When the echo intensity upon low-pressure wave emission is higher than the predetermined threshold, the impulse is emitted at a timing determined by the irradiating interval. After that, even if the echo intensity is higher than the threshold and the focal point coincides with the stone, a subsequent impulse is not emitted until a time corresponding to the irradiating interval elapses.

When the echo intensity upon low-pressure wave emission is lower than the threshold, i.e., when the focal point does not coincide the stone, the impulse is not emitted. However, discrimination of coincidence/non-coincidence between the focal point and the stone by means of low-voltage wave transmission and echo reception is performed at sufficiently short time intervals. Therefore, once a coincidence is discriminated, an impulse for pulverization is immediately emitted. In this case as well, once the impulse is emitted, a subsequent impulse is not emitted until a time corresponding to the predetermined irradiating interval elapses.

As a result, when the focal point and the stone do not coincide, the wait time until the subsequent impulse irradiation is shortened while the missed-shot preventive function in which the impulse does not irradiate the other normal tissue other than the stone is maintained, and the predetermined impulse irradiating rate condition is kept satisfied.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIGS. 3(a) to 3(d) are timing charts for explaining the operation of a conventional lithotrity apparatus.

DETAILED DESCRIPTION OF THE PREFERRED EMBODIMENTS

Figure 1:
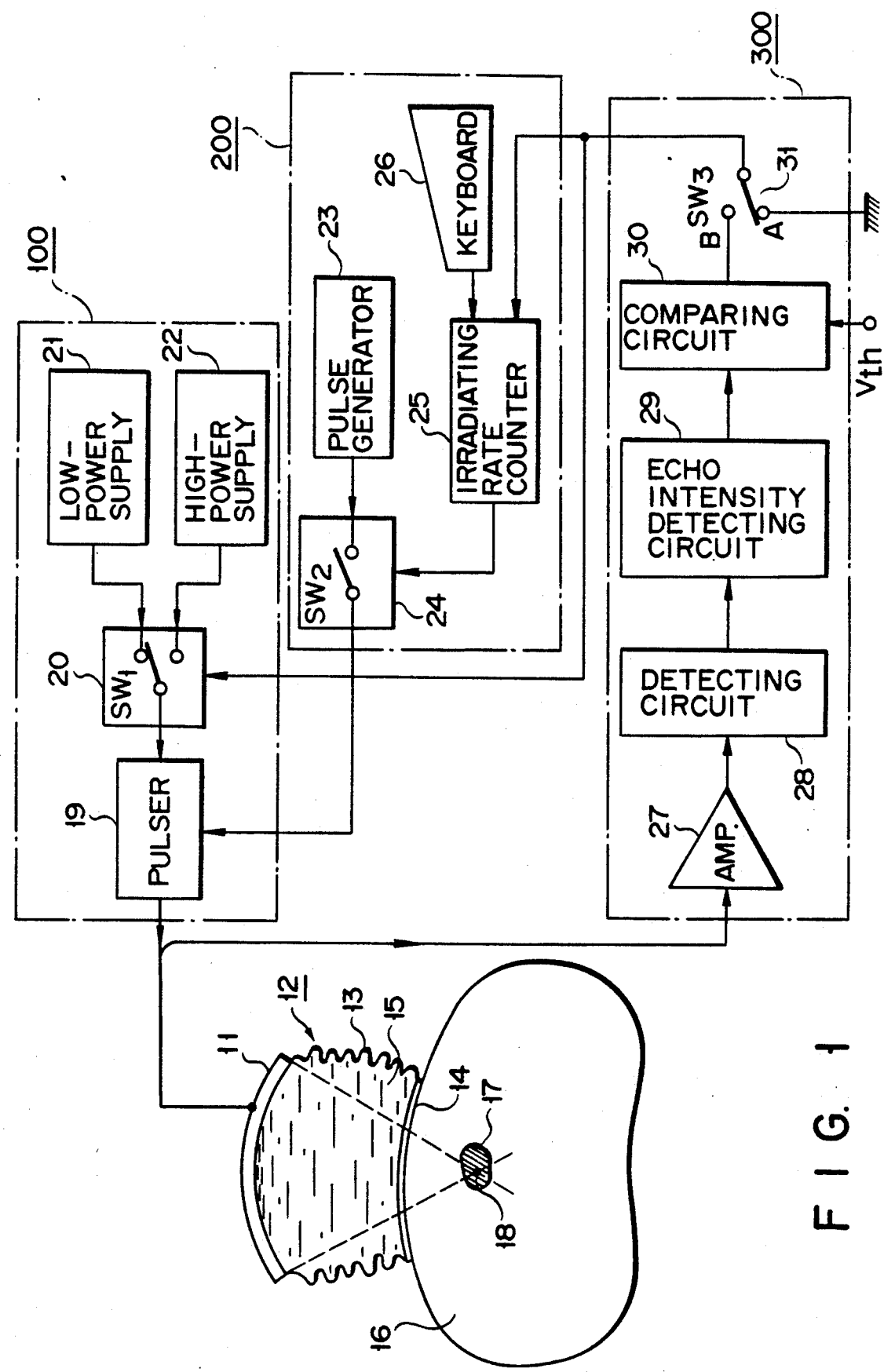
FIG. 1 is a block diagram of a lithotrity apparatus according to an embodiment of the present invention.

FIG. 1 is a block diagram of a lithotrity apparatus according to an embodiment of the present invention, and shows an example in which a piezoelectric device is used as the impulse source.

Referring to FIG. 1, an applicator comprises a piezoelectric device 11 and a coupling unit 12. The piezoelectric device 11 serves as the impulse generating source. The coupling unit 12 couples the piezoelectric device 11 with the body surface of a patient 16. The piezoelectric device 11 is a spherical shell consisting of piezoelectric device unit rings arranged concentrically.

The coupling unit 12 comprises an extendible bag-like container provided to cover a portion ahead of the piezoelectric device 11 and consisting of a bellows 13 and a body surface contact film 14. Water 15 fills the container as a liquid to cause the impulse to propagate therein. A rubber film, for example, is used as the body surface contact film 14. For treatment, the body contact film 14 is brought into contact with the body surface of the patient 16 through a coupling agent (not shown), e.g., jelly. An impulse generated by the piezoelectric device 11 passes through the water 15 in the coupling unit 12 and the body surface contact film 14 and is focused on and irradiates a stone 17 in the body of the patient 16 located at a focal point 18 of the piezoelectric device 11.

The piezoelectric device 11 is connected to a pulser 19 comprising a pulse generator. The pulser 19 is selectively connected to a low-power supply 21 and a high-power supply 22 through a switch (SW1) 20. The supplies 21 and 22 supply drive voltages to the pulser 19. A trigger signal generated by a pulse generator 23 is supplied to the pulser 19, through a switch (SW2) 24 so that the piezoelectric device 11 generates a high- or low-power pulse. More specifically, when a low-power pulse is applied to the piezoelectric device 11 by the pulser 19, the piezoelectric device 11 generates a weak ultrasonic wave (low-pressure wave). When, a high-power pulse is applied, the piezoelectric device 11 generates an impulse. The pulse generator 23 generates a trigger signal at a time interval (e.g., about 100 msec.) sufficiently shorter than a time interval (e.g., 1 sec.) corresponding to an impulse irradiating rate.

The switch 24 is turned on/off by a pulse signal generated by an irradiating rate counter 25 at a time interval corresponding to the impulse irradiating rate. An initial value (e.g., 1 sec.) corresponding to the irradiating rate is set in the irradiating rate counter 25 by an initial output from a keyboard 26, and performs down-counting. The counter 25 counts down for a time corresponding to the irradiating rate. When the count becomes 0, the counter 25 generates a pulse and supplies it to the switch 24.

The piezoelectric device 11 also receives an echo from the inside of the patient 16, and outputs the received echo as an RF signal. An amplifier 27 amplifies the RF signal. A detecting circuit 28 detects an output from the amplifier 27. An echo intensity detecting circuit 29 detects the echo intensity, e.g., a peak value of the echo sent from the focal zone, from the output of the detecting circuit 28. A comparing circuit 30 compares the echo intensity detected by the echo intensity detecting circuit 29 with a predetermined threshold Vth and outputs a comparison signal in accordance with the comparison result. An output from the comparing circuit 30 is supplied to the switch 20 and the irradiating rat counter 25 through a switch (SW3) 31. The switch 31 serves for switching between treatment preparation and treatment start modes. In the treatment preparation mode, the switch 31 is connected to a ground side A; in the treatment start mode, to an output side B of the comparing circuit 30. Upon reception of an "L" (low) level signal from the switch 31, the switch 20 is switched to the low-power supply 21 side. Upon reception of an "H" (high) level signal, it is switched to the high-power supply 22 side. The irradiating rate counter 25 starts counting upon reception of an "H" (high) level signal from the switch 31.

The operation of this embodiment will be described with reference to the timing charts of FIGS. 2(a) to 2(d). Referring to FIGS. 2(a) to 2(d), time intervals A and B indicate time periods during which the switch (SW3) 31 of FIG. 1 is connected to the A and B sides.

Figure 2A:
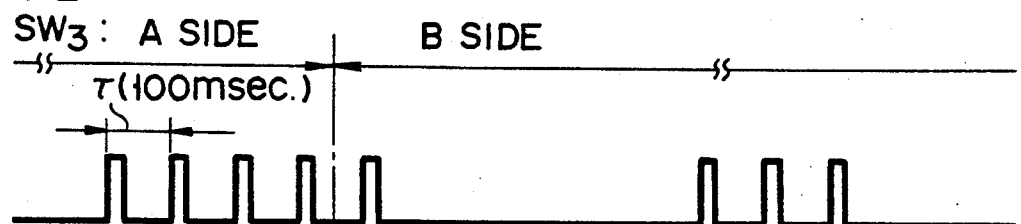
FIGS. 2(a) to 2(g) are timing charts for explaining the operation of the same.
Figure 2B:
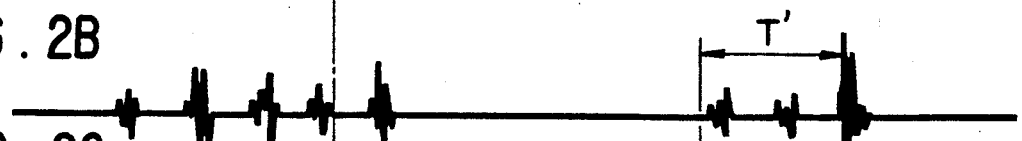
Figure 2C:
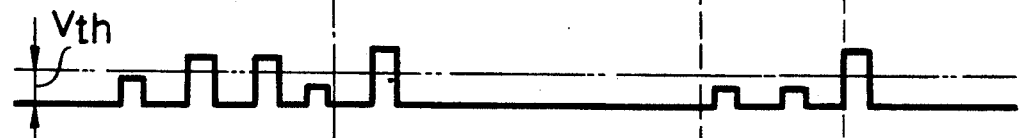

The switch 31 is first connected to the A side, and the switch (SW2) 24 is ON. Accordingly, when a trigger signal is generated by the pulse generator 23, it is supplied to the pulser 19 through the switch 24, and the pulser 19 is activated. The trigger signal supplied to the pulser 19 is a pulse signal having a time interval $\tau = 100$ msec., as shown in FIG. 2(a). The pulser 19 generates a low-power pulse since it is connected to the low-power supply 21 through the switch (SW1) 20. As a result, the piezoelectric device 11 generates a weak ultrasonic wave (low-pressure wave) weaker than an impulse toward the interior of the patient 16 through the coupling unit 12. The low-pressure wave irradiating the interior of the body is reflected at a portion having an acoustic impedance different from other portion. The echo is received by the piezoelectric device 11 and output as an RF signal. The RF signal is amplified by the amplifier 27, detected by the detecting circuit 28 as a waveform shown in FIG. 2(b), and input to the echo intensity detecting circuit 29. The echo intensity detecting circuit 29 comprises, e.g., a peak-hold circuit. The echo intensity detecting circuit 29 detects the intensity, e.g., a peak value, of the echo sent from the vicinity of the focal point 18, and outputs the detected value to the comparing circuit 30. FIG. 2(c) shows the output waveform of the echo intensity detecting circuit 29.

Figure 2D:

The comparing circuit 30 compares the output from the echo intensity detecting circuit 29 with the threshold Vth indicated as an alternate long and two short dashes line in FIG. 2(c) to discriminate coincidence between the focal point 18 and the stone 17, and outputs a comparison output having a waveform shown in FIG. 2(d). The acoustic impedance of the stone 17 is different from that of kidney tissues and the like. Therefore, the echo intensity becomes high in this case. The threshold Vth is set to almost the same level as that of the intensity of the echo sent from a kidney tissue which is measured in advance in an experiment using an animal. The threshold Vth is adjusted as required based on the experiments of the operator such as a doctor. When the echo intensity is higher than the threshold Vth, the comparing circuit 30 discriminates that the focal point 18 coincides with the stone 17.

Prior to start of lithotrity treatment, first, the operator sets an impulse irradiating rate through the keyboard as the initial value of the irradiating rate counter 25. The impulse irradiating rate is determined considering two points: (1) the patient may not feel pain due to the impulse; (2) the normal tissue must be prevented from being damaged. In general, the rate value is about 1 to 3 Hz, or more suitably, e.g., about 1 Hz. In this case, a digital value corresponding to the time of 1 sec. is set in the irradiating rate counter 25 as the initial value by the keyboard 26.

Figure 2E:
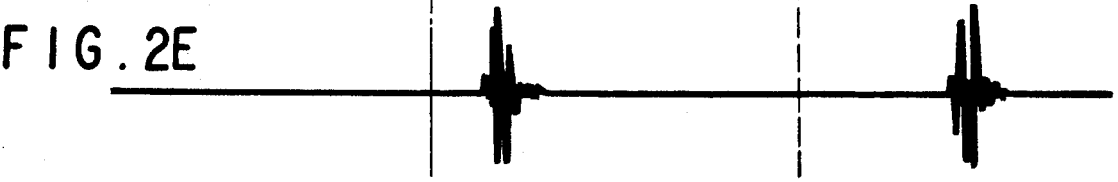

Subsequently, when lithotrity treatment is to be started, the switch 31 is switched to the B side manually, or by an interlocked operation. When it is discriminated by the comparing circuit 30 that the echo intensity is threshold Vth or more and that the focal point 18 coincides with the stone, the switch 20 is switched to the high-power supply 22 side. The pulser 19 then generates a high-power pulse in synchronism with the trigger signal shown in FIG. 2(a). As a result, an intense impulse as shown in FIG. 2(e) is generated by the piezoelectric device 11 and irradiates the stone 17 (time point: t1).

Figure 2F:
Figure 2G:
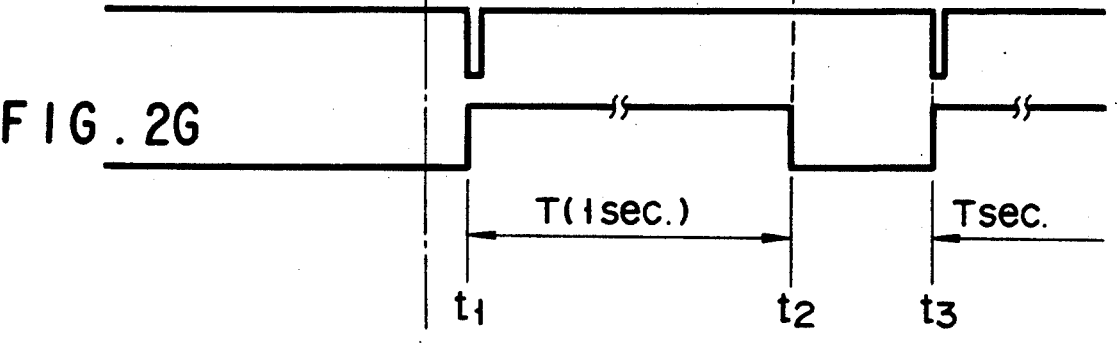

When the impulse is emitted, simultaneously a count start designating signal shown in FIG. 2(f) is supplied from the comparing circuit 30 to the irradiating rate counter 25 through the switch 31. Then, the irradiating rate counter 25 starts counting for a time T=1 sec. and keeps the switch 24 in an OFF state. FIG. 2(g) shows an output waveform of the irradiating rate counter 25. When the output is "H" level, the switch 24 is OFF. During this OFF period, even if the comparing circuit 30 discriminates positional coincidence between the focal point 18 and the stone 17, no trigger signal is supplied to the pulser 19. Therefore, the pulser 19 does not generate a high-power pulse. Accordingly, once an impulse is emitted, the subsequent impulse emission is prohibited for 1 sec.

When 1 sec. elapses after impulse irradiation (time point: t2), the switch 24 is turned on by the output from the irradiating rate counter 25. Therefore, the same operation as described above is repeated. At this time point, when the comparing circuit 30 does not discriminate a positional coincidence between the focal point 18 and the stone 17, no impulse is emitted. In this case, a subsequent impulse need not wait for a time of 1 sec. but is emitted immediately after the coincidence between the focal point 18 and the stone 17 is discriminated.

More specifically, when a time of T=1 sec. elapses after an impulse is emitted, the switch 24 is turned on, so that low-pressure wave emission, its echo reception, echo intensity detection, and the discrimination of the positional coincidence by comparison of the focal point 18 and the stone 17 are repeated at short time intervals $\tau = 100$ ms based on trigger signals from the pulse generator. When the focal point 18 coincides with the stone 17, the switch 20 is switched to the high-power supply 22 side, the pulser 19 generates a high-power pulse, and an impulse is emitted. Therefore, referring to FIG. 2, when a first impulse is emitted and then a third low-pressure wave is emitted for 1 sec. after this, the detected echo intensity is the threshold Vth or higher, and it is discriminated that the focal point 18 coincides with the stone 17. Hence, the first impulse is emitted, 1 second elapses (time point t2), and at a time point t3 when 300 msec. elapses after this, the second impulse is emitted. As a result, a time period corresponding to 700 msec. conventionally required before the second impulse emission is shortened.

In this embodiment, after impulse emission, the subsequent impulse emission is prohibited during a time interval corresponding to the irradiating rate, and the discriminating operation of coincidence/non-coincidence between the focal point and the stone is also temporarily stopped. However, as a modification, the discriminating operation may be performed without interruption and only impulse emission may be prohibited.

In this embodiment, a peak value is detected to detect the echo intensity. However, for example, an integral of an echo sent from a focal zone may be calculated to obtain the echo intensity.

In this embodiment, a piezoelectric device is used as the impulse source. However, another impulse source such as underwater discharge, electromagnetic induction, micro explosion, or the like can be used instead. In this case, an ultrasonic probe may be used exclusively for discriminating a coincidence/non-coincidence between the focal point and the stone. The impulse source may be driven by a low voltage to generate a low-pressure wave, and the echo of the impulse may be received by a piezoelectric device or the like.

Various changes and modifications can be made without departing from the spirit and scope of the present invention.

According to the present invention, an impulse can irradiate only a stone by preventing a missed-shot to a normal tissue while a predetermined impulse irradiating rate is observed. When the focal point and the stone do not positionally coincide, a wait time until the subsequent impulse emission is shortened. As a result, efficient lithotrity treatment can be performed within a minimum treatment time.

Additional advantages and modifications will readily occur to those skilled in the art. Therefore, the invention in its broader aspects is not limited to the specific details, and representative devices, shown and described herein. Accordingly, various modifications may be without departing from the spirit or scope of the general inventive concept as defined by the appended claims and their equivalents.

What is claimed is:

1. A lithotrity apparatus for pulverizing a stone in a patient's body by irradiating the stone with an impulse having a predetermined pressure generated outside the patient's body at a predetermined irradiating time interval, comprising:
   sending means for sending a low-pressure wave, lower in pressure than the pressure of an impulse, into the patient's body at a time interval shorter than a predetermined irradiating time interval;
   receiving means for receiving an echo of the low-pressure wave sent by said sending means;
   echo intensity detecting means for detecting an intensity of the echo received by said receiving means;
   impulse emitting means for emitting an impulse when the echo intensity detected by said echo intensity detecting means is not less than a predetermined threshold; and
   irradiation prohibiting means for prohibiting emission of a further impulse by the impulse emitting means until a time corresponding to the predetermined irradiating interval elapses.

2. A lithotrity apparatus for pulverizing a stone in a patient's body by irradiating the stone with an impulse, comprising:
   a piezoelectric device sending means for sending said piezoelectric device by a low-power pulse at a shorter time interval than a predetermined irradiating time interval, the lower power pulse driving said piezoelectric device to send a low-pressure wave, lower in pressure than a predefined pressure of an impulse for irradiating and pulverizing the stone, into a patient's body;
   receiving means for receiving an echo of the low-pressure wave sent by said piezoelectric device;
   echo intensity detecting means for detecting an intensity of the echo received by said receiving means;
   impulse emitting means for driving said piezoelectric device by a high-power pulse to emit an impulse when the echo intensity detected by said echo intensity detecting means is not less than a predetermined threshold; and
   drive prohibiting means for prohibiting further driving of said piezoelectric device by a high-power pulse until a time corresponding to the predetermined irradiating time interval elapses.

3. A lithotrity apparatus comprising:
   pulse sending/receiving means comprising a piezoelectric device for emitting an impulse for lithotrity and a low-pressure wave for stone search, receiving an echo reflected from an interior of a body of a patient, and outputting the echo as a RF signal;
   sending pulse supply means for supplying a predetermined pulse having a predetermined voltage to said piezoelectric device for emitting impulses and low pressure waves;
   an irradiating rate control means;
   reception comparing processing means for receiving the RF signal from the pulse sending/receiving means, performing a comparison processing of an intensity of the received RF signal with a predetermined threshold thereby obtaining a comparison processing result, selectively outputting, in accordance with the comparison processing result, to said sending pulse supplying means, a power select signal and sending a start count signal to said irradiating rate control means in accordance with the comparison processing result; and
   wherein said irradiating rate control means controls an irradiating timing every predetermined irradiating interval in accordance with the start count signal from said reception comparing processing means.

4. An apparatus according to claim 3, wherein said sending pulse supply means comprises:
   a pulser, connected to said piezoelectric device, for supplying the predetermined pulse to said piezoelectric device in accordance with a drive voltage,
   a first switch connected to said pulser, and
   a low-power supply and a high-power supply selectively connected to said first switch for supplying the drive voltage to said pulser,
   said first switch selectively switching said pulse to said low-power supply and said high-power supply to vary the drive voltage in accordance with the power select signal from said reception comparing processing means.

5. An apparatus according to claim 3, wherein said reception comparing processing means comprises:
   an amplifier for amplifying the RF signal received from said piezoelectric device and producing an output,
   a detecting circuit for detecting the output from said amplifier,
   an echo intensity detecting circuit for detecting a peak value of the RF signal, representing an intensity reflected from a focal zone,
   a comparing circuit for comparing the peak value of the RF signal detected by said echo intensity detecting circuit with the predetermined threshold, and outputting the power select signal and the start count signal in accordance with the comparison result, and
   a first switch selectively connected to said reception comparing processing means and said sending-/receiving means,
   said first switch supplying the power select signal and the start count signal as an output instruction signal from said comparing circuit to an irradiating rate counter and a switch in the sending pulse supply means for selectively switching the pulse sending-/receiving means to a lower power supply and a high power supply only when preparation for impulse emission is completed.

6. An apparatus according to claim 3, wherein the irradiating rate control means comprises:
   a keyboard for inputting the predetermined irradiating rate interval designating a minimum time interval between impulses,
   a pulse generator for generating pulses at a rate faster than the predetermined irradiating rate interval,
   a switch means for selectively connecting said pulse generator and a pulser in the sending pulse supply means in accordance with the start count signal from said reception comparing processing means, and
   an irradiating rate counter means having an irradiating rate, in which an initial value is set in accordance with the predetermined irradiating rate interval input from said keyboard, which counts time for a time period in accordance with the irradiating rate, and which generates a designation signal for connecting and disconnecting said pulse generator and said pulser to said switch means when the count thereof reaches a predetermined value, said irradiating rate counter means starts counting upon reception of the start count signal sent from said reception comparing processing means to the irradiating rate control means and said switch means is off until a time period corresponding to the irradiating rate elapses.

7. A lithotrity apparatus for pulverizing an object in a patient's body comprising:

a first sending means for sending analysis waves into a patient's body;

a receiving means for receiving echoes of analysis waves, the received echoes each having an intensity;

an echo intensity detecting means connected to the receiving means for detecting intensities of received echoes;

a comparing means for comparing echo intensities with a predefined echo threshold and outputting a detection signal only when an echo of an analysis wave is stronger than the predetermined echo threshold;

a first timing means for outputting a first timing signal having a first predefined time period;

a first engaging means for engaging said first sending means to send analysis waves in response to the first timer signal;

a second sending means for sending a first and subsequent destruction waves into a patient's body;

a second engaging means for engaging said second sending means for sending a first destructive wave into a patient's body in response to the detection signal;

a second timing means for outputting a second timing signal, said timing means counts down for a second predetermined time period which is longer than the first predefined time period and outputs a second timing signal after the second predefined time period has counted down;

a start means for starting the second timer means each time a destructive wave is sent;

a third engaging means for engaging said second sending means to send a subsequent destruction wave into a patient's body when both the second timing signal is output and the comparing means outputs a detection signal after a last sent analysis wave.

8. A lithotrity apparatus according to claim 7, wherein the time period of the second timer means is longer than twice the time period of the first timer means.

9. A lithotrity apparatus according to claim 7, wherein the time period of the second timer means is longer than or equal to 10 times the time period of the first timer means.

* * * * *